United States Patent
Olmstead

(10) Patent No.: US 6,485,711 B1
(45) Date of Patent: Nov. 26, 2002

(54) ORGANIC TOOTHPASTE CONTAINING SAPONIN

(76) Inventor: Michael J. Olmstead, 2658 del Mar Heights, Del Mar, CA (US) 92014

( * ) Notice: Subject to any disclaimer, the term of this patent is extended or adjusted under 35 U.S.C. 154(b) by 0 days.

(21) Appl. No.: 10/104,716

(22) Filed: Mar. 21, 2002

(51) Int. Cl.$^7$ .............................. A61K 7/16; A61K 7/26; A61K 35/78
(52) U.S. Cl. .................. 424/58; 424/49; 424/195.1; 514/783
(58) Field of Search ..................................... 424/49–58

(56) References Cited

U.S. PATENT DOCUMENTS

| | | | |
|---|---|---|---|
| 3,883,425 A | | 5/1975 | Dorn |
| 4,082,841 A | * | 4/1978 | Pader ........................... 424/50 |
| 4,167,559 A | * | 9/1979 | Michel ......................... 424/58 |
| 4,358,286 A | | 11/1982 | Grollier et al. |
| 4,460,488 A | | 7/1984 | Grollier et al. |
| 4,508,714 A | | 4/1985 | Cecic et al. |
| 4,800,080 A | | 1/1989 | Grollier et al. |
| 5,043,153 A | * | 8/1991 | Vioeki et al. .................. 424/49 |
| 5,130,122 A | * | 7/1992 | Tabibi et al. .................. 424/49 |
| 5,294,434 A | * | 3/1994 | King et al. .................... 424/58 |
| 5,376,374 A | * | 12/1994 | Zelaya ..................... 424/195.1 |
| 5,378,465 A | * | 1/1995 | Zeines ..................... 424/195.1 |
| 5,425,944 A | * | 6/1995 | Harich ..................... 424/195.1 |
| 5,466,443 A | * | 11/1995 | Ho et al. ................. 424/195.1 |
| 5,503,766 A | | 4/1996 | Kulperger |
| 5,503,822 A | * | 4/1996 | Schulman ..................... 424/49 |
| 5,631,001 A | * | 5/1997 | Harich et al. .................. 424/58 |
| 5,980,870 A | * | 11/1999 | Baik et al. ..................... 424/58 |
| 6,063,382 A | | 5/2000 | Nakajima et al. |
| 6,153,208 A | | 11/2000 | McAtee et al. |
| 6,190,678 B1 | | 2/2001 | Hasenoehrl et al. |
| 6,193,986 B1 | | 2/2001 | Sakurada |
| 6,197,755 B1 | | 3/2001 | Carrano et al. |
| 6,241,975 B1 | * | 6/2001 | Moon et al. ................... 424/58 |
| 6,309,675 B1 | | 10/2001 | Sobczak |
| 6,338,855 B1 | | 1/2002 | Albacarys et al. |

FOREIGN PATENT DOCUMENTS

| | | | |
|---|---|---|---|
| CN | 1111123 A | * | 11/1995 |
| DE | 1952263J A1 | * | 1/1997 |
| EP | 1126759 A1 | * | 8/2001 |
| JP | 360013707 A | * | 1/1985 |
| JP | 04124197 A | * | 4/1992 |
| JP | 7-107922 | | 4/1995 |
| JP | 2000128753 A | * | 5/2000 |
| WO | WO 96/00563 | | 1/1996 |
| WO | 99 43293 A1 | * | 9/1999 |

* cited by examiner

*Primary Examiner*—Shep K. Rose
(74) *Attorney, Agent, or Firm*—Lawrence E. Laubscher, Jr.

(57) ABSTRACT

A unique organic toothpaste characterized by the use of saponin as the cleansing/foaming agent. The saponin is a refined product derived from the bark of the Quillaja and/or Yucca tree and its content may form up to 10% by weight of the toothpaste. Other organic products for whitening teeth, soothing irritated gums or other tissues, and fighting microbes are also provided.

17 Claims, No Drawings

ORGANIC TOOTHPASTE CONTAINING SAPONIN

BACKGROUND OF THE INVENTION

The vast majority of oral care products on the market today are synthetic or comprise a majority of synthetic ingredients. Some synthetic ingredients are carcinogenic when presented in high dosages or concentrations. Others induce allergic reactions in many people. In some instances, ingredients can substantially increase the occurrence of apthatos ulcerations. Accordingly, there is a trend toward natural, organic products not only in foods but also in oral care products such as mouthwash and toothpaste. The present invention relates to a new and unique organic toothpaste or dentifrice which performs as well or better than synthetic toothpastes but contains none of the risks inherent with artificial and synthetic oral care products. The product described contains significant levels of natural substances that will help to control the oral bacteria that are associated with many larger health issues (heart disease, stroke, abnormal pregnancy outcomes, etc.) The toothpaste according to the invention contains saponin which acts as a surfactant to produce adequate foaming for cleansing the teeth.

BRIEF DESCRIPTION OF THE PRIOR ART

"Natural" toothpastes are well known in the oral care industry. For example, toothpaste containing baking soda has been used for many years. A major drawback of the prior "natural" toothpastes is that they do not perform satisfactorily. That is, a high concentration of baking soda is required to provide adequate cleaning. However, such high concentrations are distasteful and overly abrasive, thus the baking soda toothpastes on the market have insufficient quantities of cleaning agent and high concentrations of flavoring to make them acceptable to consumers.

It is known to use saponins in personal care products such as cosmetics as shown by the Grollier et al. U.S. Pat. No. 4,800,080 and scalp lotions as shown by the Cecic et al. U.S. Pat. No. 4,508,714. In addition, it is known to use yucca extract as a deodorizing breath composition as disclosed in the Michel U.S. Pat. No. 4,167,559. However, it is not known in the relevant art to use saponins as the primary cleansing ingredient in toothpaste.

SUMMARY OF THE INVENTION

Accordingly, it is a primary object of the present invention to provide an organic toothpaste comprising a mixture of natural ingredients and 0.01–10% by weight of saponin as a surfactant foaming agent. The saponin is preferably derived from Quillaja or Yucca and is refined to a content of 50–100% from Quillaja or 30–100% from Yucca.

According to a further object of the invention, the toothpaste includes 30–60% by weight of vegetable glycerine as a moisturizer.

According to a more specific object of the invention, the natural ingredients include one or more of the following: calcium carbonate for a whitener/mineralizer, distilled water for a moisturizer, aloe vera for soothing irritated gums, silica for a whitener/mineralizer, baking soda for an acid neutralizer, Irish moss for a thickener and to soothe irritated gums, peppermint for flavor and breath freshener, Manuka oil for an anti-bacterial agent, grapefruit seed extract for an anti-microbial agent, and green papaya for a cleanser,

DETAILED DESCRIPTION

The organic toothpaste of the present invention is characterized by the use of saponin as a surfactant/foaming agent which is the primary cleaning ingredient. Saponins are found in different plants including the bark of Quillaja (or Quillaia) which is also referred to as soap bark, Quillaja Saponaria Molina, or Chilean Soap Bark Tree. Saponin is also found in the bark of the Yucca tree, also known as Yucca Shidigera, Mohave Extract, Joshua Tree and Adam's Needle. Quillija is the preferred source of saponin because of the high levels of saponin contained therein, although saponin from Yucca or from a combination of Quillaja and Yucca may be used as well.

Saponins have been approved by the U.S. Food and Drug Administration as a food and beverage flavor. While saponin contributes to the flavor of the inventive toothpaste, its primary function is that it produces foaming without the use of synthetic surfactants. Avoiding the use of synthetic components while providing superior cleaning attributes is an important feature of the toothpaste.

The toothpaste according to the invention includes 0.1–10% by weight of saponin, and preferably 1%. The saponin is preferably refined from Quillaja extract with a total saponin content from 50–100% and/or Yucca extract with a total saponin content of 30–100%. The use of refined saponin prevents certain chemicals from being included in the toothpaste which degrade over a very short time period (just a few weeks) to discolor the product. In addition, refined saponins enhance the flavor and taste of the toothpaste when compared to a product with unrefined saponin which is very bitter.

The bulk of the toothpaste comprises a moisturizer or humectant. Preferably, the humectant is vegetable glycerin comprising 30–60% by weight of the product. This can be obtained from kosher, pesticide-free palm kemal oil.

The remaining ingredients of the toothpaste are organic products which provide other desirable benefits. The following chart lists the additional ingredients in the preferred composition of the toothpaste. For each ingredient, the preferred percentage by weight, purpose, and source are also provided:

| Ingredient | Percentage | Purpose | Source |
| --- | --- | --- | --- |
| Calcium carbonate | 15–50% | Whitener/mineralization | Mineral |
| Distilled water | 3–18% | Moisturizer | Distilled |
| Aloe Vera juice | 0.5–20% | Soothe irritated tissue | Organic |
| Fumed silica | 0.1–7% | Whitener/mineralization | Mineral |
| Hydrated silica | 0.5–10% | Whitener/mineralization | Mineral |
| Baking Soda | 0.5–8% | Acid neutralizer | Mineral |
| Carrageenan/Irish Moss | 0.1–3% | Thickener/soothe irritated tissue | Ocean harvested kelp |
| Peppermint oil | 0.1–2% | Flavor | Organic |
| Manuka oil/Leptospermum Scoparium oil/deodorized Manuka oil | 0.5–2% | Anti-microbial | Wild harvested native New Zealand plant |
| Grapefruit seed extract | 0.1–3% | Anti-microbial | Organic |
| Green papaya extract/green papaya, carica papaya | 0.01–2% | Cleanser | Organic |

It will be appreciated by those of ordinary skill in the art that it is not necessary to include each of the ingredients listed above in the saponin-containing toothpaste according to the invention. Certain ingredients may be eliminated, as desired, to create cleansing dentifrices with different attributes.

Set forth below is a list of ingredients in their levels of concentration according to a preferred embodiment of the invention. The percentages are based on a 100 g sample and are by weight in grams.

| Ingredient | Percentage |
| --- | --- |
| Vegetable glycerin | 46.570 |
| Calcium carbonate | 26.000 |
| Water | 9.370 |
| Aloe vera juice | 6.000 |
| Fumed silica | 1.650 |
| Hydrated silica | 4.300 |
| Baking soda | 2.200 |
| Quillaja | 1.000 |
| Carrageenan | .715 |
| Peppermint oil | .820 |
| Manuka oil | .600 |
| Grapefruit seed extract | .375 |
| Green papaya extract | .400 |

The toothpaste containing the above ingredients is unique because it contains therapeutic materials as well as certified organic or wild harvested ingredients which are tolerant for most individuals. These attributes cooperate with the unique cleansing action of saponin to provide a healthy and effective dentifrice.

While the preferred forms and embodiments of the invention have been described, it will be apparent to those of ordinary skill in the art that various changes and modifications may be made without deviating from the inventive concepts set forth above.

What is claimed is:

1. An organic natural toothpaste, comprising a mixture of natural ingredients and 0.01–10% by weight of refined saponin as a primary surfactant foaming agent free of synthetic surfactants, anti-microbial agents and cleansers and thereby containing none of the risks inherent with artificial and synthetic surfactants, anti-microbial agents and cleansers in oral care products, said refined saponins enhancing the flavor and taste when compared to bitter tasting unrefined saponin.

2. An organic natural toothpaste as defined in claim 1, wherein said saponin is derived from at least one of Quillaja and Yucca.

3. An organic natural toothpaste as defined in claim 2, arid further comprising 30–60% by weight of vegetable glycerin refined from Kosher pesticide-free vegetable oil as a moisturizer.

4. An organic natural toothpaste as defined in claim 2, wherein said natural ingredients include 15–50% by weight of calcium carbonate as a whitener mineralizer.

5. An organic natural toothpaste as defined in claim 2, wherein said natural ingredients include 3–18% by weight of distilled water as a moisturizer.

6. An organic natural toothpaste as defined in claim 2, wherein said natural ingredients include 0.05–20% by weight of aloe vera juice for soothing irritated gums.

7. An organic natural toothpaste as defined in claim 2, wherein said natural ingredients include at least one of 0.1–7% by weight of fumed silica and 0.5–10% by weight of hydrated silica as a whitener/mineralizer.

8. An organic natural toothpaste as defined in claim 2, wherein said natural ingredients include 0.5–8% by weight of baking soda as an acid neutralizer.

9. An organic natural toothpaste as defined in claim 2, wherein said natural ingredients include 0.01–3% by weight of carrageenan or Irish moss as a thickener and to soothe irritated gums.

10. An organic natural toothpaste as defined in claim 2, wherein said natural ingredients include 0.1–2% by weight of peppermint oil for flavoring and freshening breath.

11. An organic natural toothpaste as defined in claim 2, wherein said natural ingredients include 0.05–2% by weight of at least one of Manuka oil, Leptospermum Scoparium oil, and deodorized Manuka oil as an anti-microbial agent.

12. An organic natural toothpaste as defined in claim 2, wherein said natural ingredients include 0.1–3% by weight of grapefruit seed extract as an anti-microbial agent.

13. An organic natural toothpaste as defined in claim 2, wherein said natural ingredients include 0.01–2% by weight of at least one of green papaya extract, green papaya and Carica papaya as a cleanser.

14. An organic natural toothpaste as defined in claim 2, wherein said saponin is refined from both Quillaja and Yucca.

15. An organic natural toothpaste as defined in claim 14, wherein said Quillaja has a total saponin content of 50–100% and said Yucca has a total saponin content of 30–100%.

16. An organic natural toothpaste as defined in claim 15, and further comprising 30–60% by weight vegetable glycerin refined from Kosher pesticide-free palm kernel oil.

17. An organic natural toothpaste as defined in claim 16, wherein said natural ingredients include at least one of a) 15–50% by weight calcium carbonate;

b) 3–18% by weight distilled water;

c) 0.05–20% by weight aloe vera juice;

d) 0.1–7% by weight fumed silica;

e) 0.5–10% by weight hydrated silica;

f) 0.5–8% by weight baking soda;

g) 0.1–3% by weight of at least one of carrageenan or Irish moss;

h) 0.1–2% by weight peppermint oil;

i) 0.05–2% by weight of at least one of Manuka oil, Leptospermum Scoparium oil and deodorized Manuka oil;

j) 0.1–3% by weight grapefruit seed extract; and k) 0.01–2% by weight of at least one of green papaya extract, green papaya, and Carica papaya.

* * * * *